United States Patent [19]

Carleton et al.

[11] 4,278,870
[45] Jul. 14, 1981

[54] DENTAL MIRROR WARMER

[76] Inventors: John S. Carleton, 2009 Belmeade, Brownwood, Tex. 76801; Karl A. Senghaas, 434 Forest Hill Dr., San Antonio, Tex. 78209

[21] Appl. No.: 55,172

[22] Filed: Jul. 6, 1979

[51] Int. Cl.³ .................... H05B 1/02; A61B 1/24
[52] U.S. Cl. ................................ 219/219; 34/53; 34/202; 219/218; 219/242; 219/419; 219/502; 219/518; 219/521; 250/221; 250/222 R; 250/224; 312/209; 312/236; 350/61; 350/66; 433/30; 433/32
[58] Field of Search ............... 219/200, 201, 218, 242, 219/385, 415–419, 520, 521, 219, 518, 502; 34/201, 202, 243 R, 53; 433/30, 31, 32; 250/215, 221, 224, 222 R, 239; 350/61, 66; 312/209, 236

[56] References Cited

U.S. PATENT DOCUMENTS

| 281,224 | 7/1883 | Goodsell et al. | 219/219 X |
|---|---|---|---|
| 709,812 | 9/1902 | Bennett et al. | 219/219 X |
| 1,061,289 | 5/1913 | Heyder | 219/521 |
| 1,824,310 | 9/1931 | Thompson | 219/521 X |
| 1,843,067 | 1/1932 | De Terra | 219/219 X |
| 1,934,110 | 11/1933 | Wilson | 219/219 X |
| 2,120,091 | 6/1938 | Densten | 219/219 X |
| 2,180,213 | 11/1939 | Peake | 219/521 X |
| 2,471,884 | 5/1949 | Monnot | 219/218 |
| 2,527,049 | 10/1950 | Aagesen | 219/385 |
| 2,606,274 | 8/1952 | Spierer | 250/221 X |
| 2,611,097 | 9/1952 | Stanley et al. | 250/224 |
| 2,616,269 | 11/1952 | Reynolds | 219/218 X |
| 2,625,858 | 1/1953 | Dreher | 350/61 |
| 2,777,934 | 1/1957 | Falkenthal | 250/221 X |
| 2,856,501 | 10/1958 | Kueser | 219/402 |
| 2,999,145 | 9/1961 | Espenhain | 219/218 X |
| 3,278,256 | 10/1966 | Skaller | 219/369 X |
| 3,353,905 | 11/1967 | Ellis | 422/291 |
| 3,466,752 | 9/1969 | Braun | 219/242 X |
| 3,637,982 | 1/1972 | Reaves | 219/221 X |
| 3,643,346 | 2/1972 | Lester | 34/202 |
| 3,689,735 | 9/1972 | McLeod et al. | 219/518 X |
| 3,703,634 | 11/1972 | Buckey | 219/242 X |
| 3,776,694 | 12/1973 | Leittl | 312/209 X |
| 3,820,251 | 6/1974 | Abernathy | 219/521 X |
| 3,961,893 | 6/1976 | Russell et al. | 219/401 X |
| 4,013,886 | 3/1977 | Schmid | 250/221 |

Primary Examiner—A. Bartis
Attorney, Agent, or Firm—Roylance, Abrams, Berdo & Farley

[57] ABSTRACT

A dental mirror warmer to prevent fogging when the mirror is placed in a patient's mouth includes a housing with a cover having an opening. Below the opening is a heating well to receive the reflective end of the mirror. The well has a stainless steel wall connected to a transformer which supplies high current at low voltage to heat the wall. The supply to the transformer is controlled by a photoresponsive device responsive to insertion of the mirror and a timing circuit which permits current supply for a short heating interval. A temperature sensor shortens the interval when heating cycles are initiated frequently. The photoresponsive device is mounted in the housing in juxtaposition with a light transmissive opening in a wall of the heating well. The photoresponsive device includes a source of light arranged to direct light into the heating well through the opening and a photoresponsive element arranged to receive light reflected from the reflective surface of a mirror inserted into the heating well.

5 Claims, 7 Drawing Figures

DENTAL MIRROR WARMER

This invention relates to a device for heating dental mirrors to prevent fogging during use.

BACKGROUND OF THE INVENTION

Angled examination mirrors are commonly used by dentists during examination, prophylaxis and treatment. It has long been known that such a mirror tends to accumulate condensation when it is placed in a patient's mouth if the mirror is significantly colder before insertion than the temperature of the mouth. This tendency, known as fogging, is a nuisance to the dentist and the patient because it obscures the dentist's vision and requires that the mirror surface be wiped clean rather frequently, thereby delaying or extending the examination or treatment process. It can also be somewhat more serious than a mere nuisance if the dentist is at a critical point in a treatment procedure, and suddenly finds that he cannot properly see the subject of his efforts.

Repeated wiping of the mirror surface to remove the fog is therefore a necessity and is not only annoying, distracting and time consuming but can also represent a condition of reduced sanitation.

A readily apparent solution to the problem is to elevate the temperature of the mirror to about body temperature or slightly above. While this is, in theory, a successful solution, there has been no fully satisfactory device developed to quickly and adequately heat the mirror to the desired temperature without excessive use of energy, overheating, or excessive cost. Examples of prior art devices designed to accomplish heating of dental mirrors or heating or drying of other small devices are found in the following U.S. Patents.

Monnont (U.S. Pat. No. 2,471,884) shows a standard dentist's instrument tray which has heating elements beneath the tray to elevate its temperature so that any instrument placed thereon will be heated.

De Terra (U.S. Pat. No. 1,843,067) shows a dental mirror with a heat storage fluid to retain heat after holding the mirror in a flame.

Dreher (U.S. Pat. No. 2,625,858) shows a dental mirror with a heat conductive handle to convey body heat to the mirror.

Goodsell et al (U.S. Pat. No. 281,224), Bennett et al (U.S. Pat. No. 709,812), Wilson (U.S. Pat. No. 1,934,110) and Densten (U.S. Pat. No. 2,120,091) show dental mirrors with electric heating elements therein attached by wires to a power source.

The following patents show cabinets of various kinds for heating or sterilizing diverse items such as toothbrushes or medical implements using hot air, a heating lamp or some other form of heating means.

| | | |
|---|---|---|
| Re. | 24,738 | Kueser |
| | 1,824,310 | Thompson |
| | 2,180,213 | Peake |
| | 2,616,269 | Reynolds |
| | 2,999,145 | Espenhain |
| | 3,278,256 | Skaller |
| | 3,353,905 | Ellis |
| | 3,637,982 | Reaves |
| | 3,776,694 | Leittl |
| | 3,820,251 | Abernathy |
| | 3,961,893 | Russell et al. |

As will be seen, some previously developed solutions involve the connection of electrical power directly to the mirror. While this may adequately heat the mirror, the existence of wires to the mirror handle adds to the mirror weight and severely restricts the dentist's freedom of manipulation of the mirror, an important need. Other devices using heating elements in an instrument tray, light bulbs, and the like are quite wasteful of energy and do not provide any technique for exercising control over the ultimate temperature of the mirror or handle with the result that the mirror may not be sufficiently warmed or may be overheated to the discomfort of the patient or the dentist.

BRIEF DESCRIPTION OF THE INVENTION

An object of the present invention is to provide a device for heating a mirror to near normal body temperature quickly, i.e., within a few seconds.

A further object is to provide such a device which uses little or no energy except while heating a mirror, and which is simple, safe and reliable in construction and operation.

Yet another object is to provide a mirror warmer which includes means for limiting the warming to prevent overheating.

Briefly described, the invention includes an apparatus for warming a dental mirror before use to prevent fogging thereof comprising the combination of a housing, a heating well supported in said housing, said well having a plurality of walls at least one of which is electrically conductive and capable of generating heat when electric current is caused to flow therethrough, means in said housing defining an access opening adjacent said well for permitting insertion into the well of at least the reflective portion of said mirror, means connectable to a source of electrical power for providing electric current to said conductive wall for heating said wall, means in a wall of said well defining a light transmissive portion therethrough; photoelectric means mounted in said housing for transmitting light into said well and receiving light reflected from the reflective portion of a mirror in said well through said light transmissive portion and for producing a control signal in response to said reflected light; and circuit means responsive to said control signal for actuating said means for providing electric current to the conductive wall for a limited predetermined time interval.

In order that the manner in which the foregoing and other objects are attained in accordance with the invention can be understood in detail, a particularly advantageous embodiment thereof will be described with reference to the accompanying drawings, which form a part of the specification, and wherein.

Figure 1:
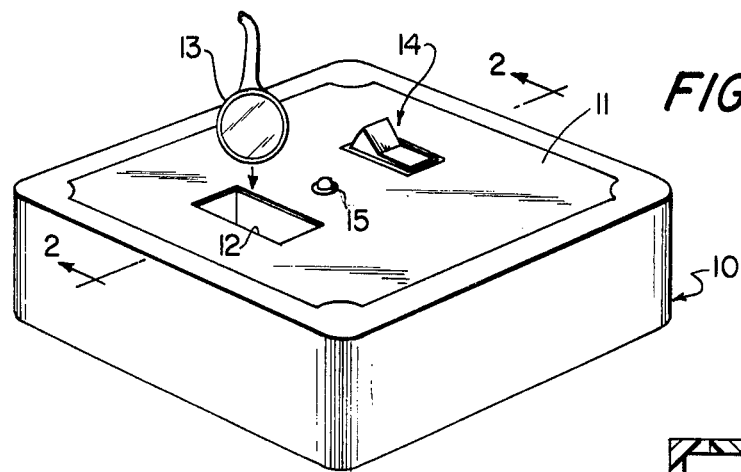
FIG. 1 is a perspective view of a dental mirror warmer in accordance with the invention.
Figure 3:
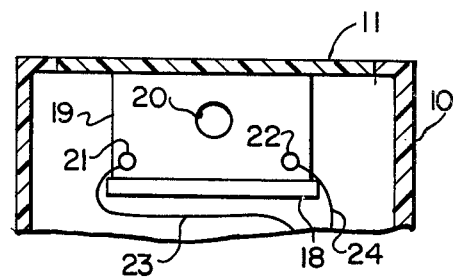
FIG. 3 is a partial front elevation along line 3—3 of FIG. 2.
Figure 2:
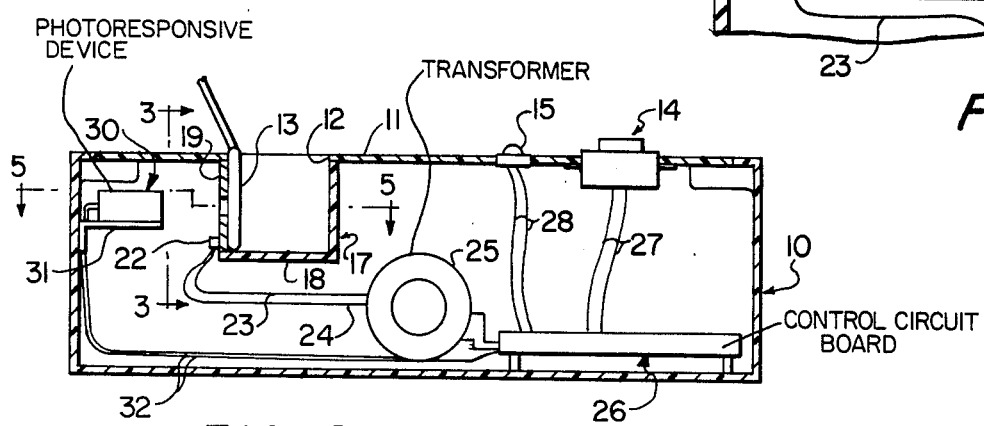
FIG. 2 is a side elevation, in section, along line 2—2 of FIG. 1 showing the interior arrangement of components.

Referring now to the drawings in detail, it will be seen from FIGS. 1 and 2 that the dental mirror warmer includes a housing indicated generally at 10 which is generally square in plan and rectangular in elevation, the housing being formed from an electrically non-conductive material such as a suitable polymeric material. The housing has an open top which is closed by a cover 11 of similar material. The cover includes a rectangular opening 12 through which the reflective portion 13 of a mirror to be warmed can be inserted. The cover also supports an on-off switch indicated generally at 14 for controlling the supply of power to the circuitry within the warming device, and an indicator light 15, which, as will be described, indicates when the apparatus is actually operating.

Figure 4:
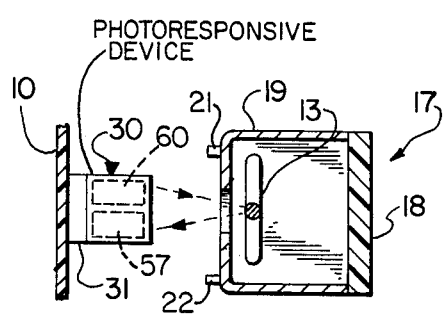
FIG. 4 is an enlarged perspective view of the heating well portion of the apparatus of FIGS. 1-3.

A heating well, which is generally in the shape of a parallelepiped, is suspended under cover 11 and depends below opening 12, the well being indicated generally at 17. As best seen in FIG. 4, the heating well is formed using two materials, one being electrically non-conductive and the other being electrically conductive. The non-conductive portion of the well comprises a generally L-shaped bracket 18 having a vertical wall and a horizontal floor and a generally U-shaped electrically conductive portion 19 which is, preferably, made using a stainless steel such as type 304 stainless or similar material. The conductive portion is conveniently formed such that, together with the vertical portion of bracket 18, it defines a substantially closed chamber being open at that top portion which aligns with opening 12. The size and shape of the heating well, along with the opening 12, is not particularly critical except that it should be large enough to receive the reflective portion of a mirror and sufficiently small to keep the mirror in relatively close proximity to the conductive portion of the device. As seen in FIG. 4, an opening 20 is formed in the wall of member 19 opposite the vertical wall of bracket 18, the purpose of the opening being to provide a light-transmissive portion for use with the photoresponsive device, to be described.

Portion 19 is also provided with means 21 and 22 for the attachment of electrical wires. As shown in FIG. 2, electrical conductors 23 and 24 are connected to these terminals and to the secondary winding of a transformer 25. The primary winding of transformer 25 is connected to circuit components on a printed circuit board 26 which is mounted in the bottom of the housing and which carries the various circuit components for the control of the apparatus which will be described in conjunction with FIG. 7. It will also be observed in FIG. 2 that switch 14 is connected to the circuit board by conductors 27 and the indicator light is also connected thereto by conductors 28.

Figure 5:
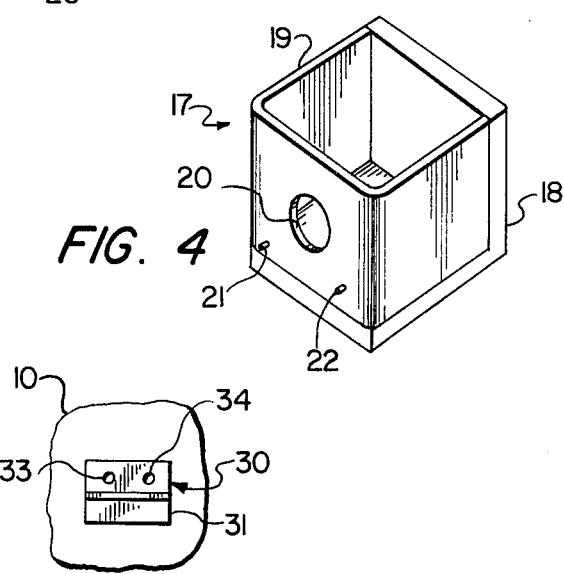
FIG. 5 is an enlarged partial sectional top plan view of the photocell and heating well portion of the apparatus of FIGS. 1-4 along line 5—5 of FIG. 2.
Figure 6:
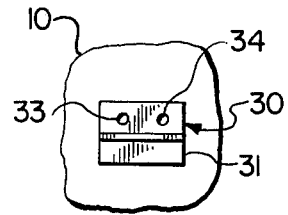
FIG. 6 is an enlarged elevation of the photoresponsive device portion of the apparatus of FIGS. 1-5.

A photoresponsive device 30 is supported on a bracket 31 attached to an end wall of the housing in a position such that it faces opening 20. The photoresponsive device is connected to the printed circuit board by conductors 32, and contains a source of light and a photoresponsive element of a type which has a conductivity characteristic depending upon light incident thereon. As seen in FIG. 6, the photoresponsive device has openings 33 and 34 facing opening 20, one of openings 33 and 34 being associated with a source of light and the other being associated with the photoconductive device. As seen in FIG. 5, light emanating from one of those openings is reflected from the reflective surface of a mirror 13 inserted into the well and the reflected light is received by the photoresponsive device behind the other opening to control the circuit, again to be described in connection with FIG. 7.

In the context of the present application, the term "light" is used to mean electromagnetic radiation in the visible portion of the spectrum as well as the spectral regions outside of the visible range. It is particularly convenient to employ a source of infrared light in the photoresponsive device 30 and to use a photosensitive element which is particularly responsive in the infrared region so that ambient light, which is often from a fluorescent source having dominant amplitudes in the shorter wavelength regions in the blue end of the visible spectrum and the ultraviolet region, from interfering with the operation of the device.

The circuit associated with printed circuit board 26 is designed to remain in a substantially dormant condition until activated by the insertion of a mirror. The only power needed is that to energize the light source in unit 30, this being supplied only when switch 14 is moved to its "on" position. When a mirror 13 is inserted into the well, light produced by the source within unit 30 is reflected to the photocell from the reflective portion of the mirror, thereby altering the conductivity condition of the photosensitive member therein and providing a signal on conductors 32 to the control circuit. The control circuit includes a bistable device which has a stable state and a temporary, unstable state similar in nature to a monostable multivibrator. When a signal is provided on conductors 32, the bistable timing circuit is caused to switch from its stable to its unstable, or temporary, state, providing voltage to the primary winding of transformer 25. The transformer is a step-down transformer having a large step-down ratio such that when the primary winding is supplied with relatively high voltage at low current, the secondary winding provides relatively high current at low voltage. The secondary winding, being connected to the conductive portion of the well structure, thus causes current to pass between terminals 21 and 22 through the conductive material of member 19, causing that member to be rapidly heated. This heat is quickly transferred to mirror 13, raising the temperature of the mirror. Supply of heating current to member 19 continues so long as the bistable timing device is in its unstable state, an interval in the order of a few seconds, e.g., 3–4 seconds. At the end of that interval, current supply to the member 19 is terminated and the system returns to its dormant state. Indicator light 15 is caused to glow only during that interval in which current is supplied to the heating wall.

Because of the fact that low voltage is supplied to the well, the opportunity for inadvertent electrical shock is substantially eliminated. Additionally, the circuit is provided with means for preventing its reenergization unless the mirror is removed from the well and reinserted, causing the initiation of a new cycle.

Figure 7:
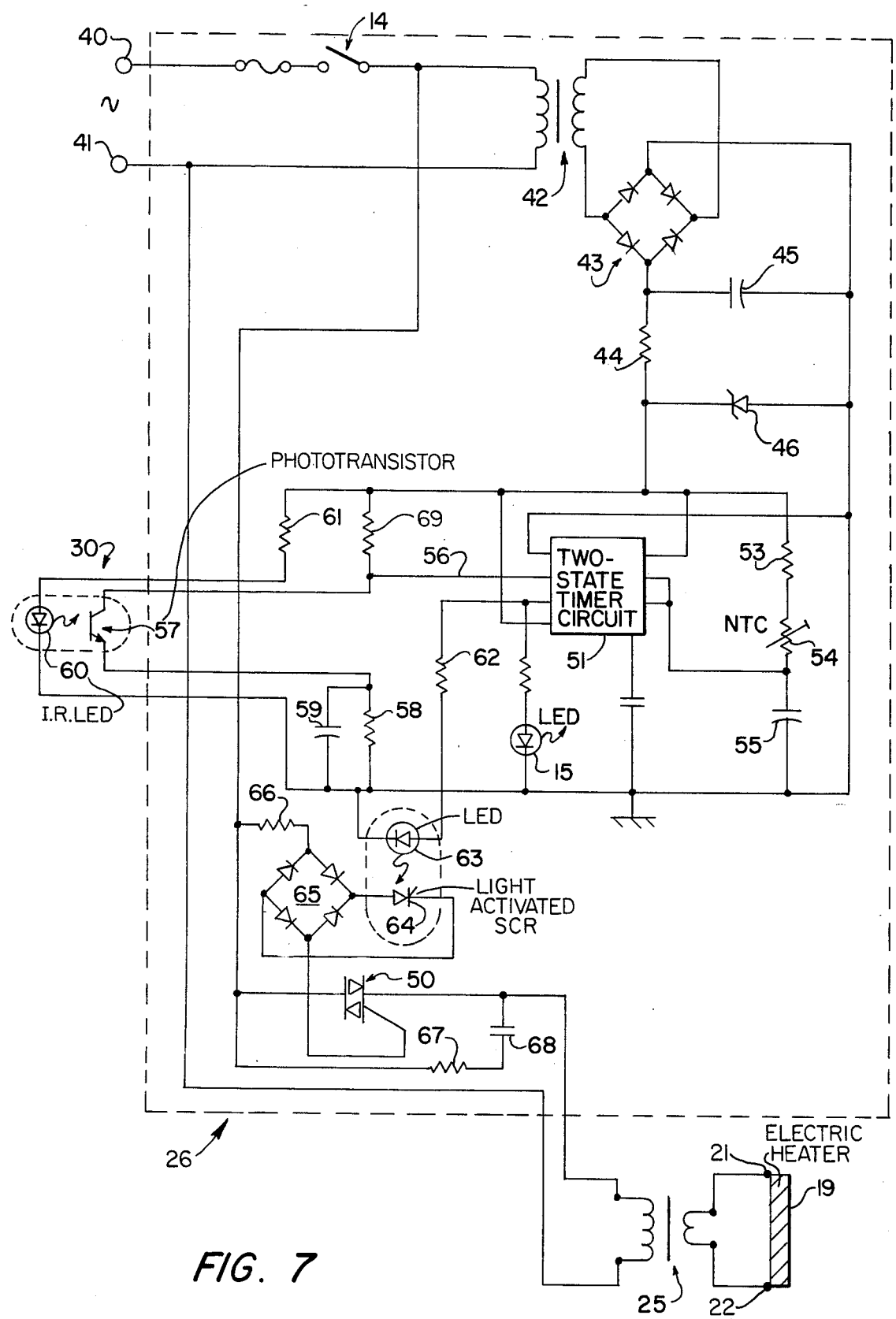
FIG. 7 is a schematic circuit diagram of a control circuit usable in the apparatus according to the invention.

Turning now to FIG. 7, it will be observed that certain components of the system are identified using the same reference numerals as in FIGS. 1–6, including switch 14, indicator light 15, conductive well member 19, transformer 25 and photoconductive unit 30. A source of line voltage at 120 volts AC is connected to power terminals 40 and 41 and, through a fuse and a switch 14, to the primary winding of a transformer 42 which is a step-down transformer providing 6 volts at its secondary winding for supply of the control circuit. The secondary winding is connected to the input terminals of a bridge rectifier circuit indicated generally at 43, the output of which is connected to a filter and voltage control circuit including a resistor 44, a parallel capacitor 45 and a Zener diode 46 which can be chosen to have a breakdown voltage of approximately 5 volts. Thus, the remainder of the control circuit is supplied with 5 volts DC.

One end of the primary winding of transformer 25 is also connected to the 120 volt AC source at terminal 41, and the other side of the AC supply, at switch 14, is connected to the other end of the primary winding through the switchable conductive path of a power Triac indicated generally at 50. It will be recognized that when Triac 50 is rendered conductive, the primary winding of transformer 25 is supplied with 120 V AC line voltage. As previously mentioned, the secondary winding of transformer 25 consists of a relatively few turns compared with the primary winding, providing approximately 0.8 volts to the conductive wall at a high current on the order of 120 amperes such that approximately 100 watts is dissipated in the heating wall, permitting rapid heating thereof.

The control circuit itself includes a two-state timer circuit 51 which can be, for example, an integrated circuit such as the LM555 produced by National Semiconductor Corp., Santa Clara, Calif. However, it will be recognized that similar circuits are available from other manufacturers, and that other models employing a lower level of power are also available. The timer circuit 51 is connected to the output of the power supply portion of the circuit, previously described, and to a series circuit including resistors 53 and 54 and a capacitor 55, connected in series circuit relationship. This resistor-capacitor circuit provides the time constant for the timer circuit which determines the interval during which the timer circuit remains in a temporary, or unstable state. It will be noted that resistor 54 is a negative temperature coefficient resistance such as a thermistor which can be thermally coupled to the heating well so that, when the temperature of the well is elevated by a heating cycle, the resistance of resistor 54 is reduced, thereby shortening the time constant and reducing the interval of time during which current will be supplied to the well in subsequent intervals. Thus, close control of the temperature to which the well is heated can be provided.

The input to the timer circuit is supplied through a conductor 56 from photoconductive element 57 in photoresponsive unit 30, the element being shown as a phototransistor. The emitter electrode of the phototransistor is connected through a parallel circuit including a resistor 58 and a capacitor 59 to the circuit common conductor. This resistor-capacitor parallel circuit performs the function of preventing recycling of the heating unless the mirror is withdrawn and restored to the heating well, as previously described. A resistor 69 is connected between the collector of the phototransistor and the supply as a bias resistor.

The light source includes an infrared light emitting diode 60 in unit 30 which is connected to the power supply through a resistor 61, the value of which is chosen to control the current level supplied to the diode.

The output of the timer circuit is connected through a resistor 62 to a light emitting diode 63, the light from which is coupled to a light activated SCR 64 which, upon receipt of light from diode 63, becomes conductive. SCR 64 is connected across the output terminals of a diode bridge circuit 65, the other terminals of which are connected through a resistor 66 to the AC supply and to the control electrode of Triac 50. Thus, when SCR is rendered conductive, current is supplied to the control electrode of Triac 50, rendering it conductive. A series circuit including a resistor 67 and a capacitor 68 are connected in parallel circuit relationship with the switchable conductive path of Triac 50 to protect the Triac from voltage surges.

From the above description, it will be recognized that closing switch 14 energizes diode 60, projecting radiation into the heating well, but that no other action takes place until a mirror is inserted into the well. At that point, reflected light is received by phototransistor 57, providing an input pulse to timer circuit 51, causing the circuit to switch to its unstable state. Circuit 51 remains in the unstable state for an interval, approximately 3-4 seconds, determined by the time constant of the series RC circuit including components 53-55, providing an output signal to diode 63 which renders SCR 64 conductive, providing a rectified signal from bridge 65 to Triac 50, switching its conductive path into a conductive state and supplying current to the primary winding of transformer 25. The secondary winding of that transformer then supplies current at approximately 120 amperes and 0.8 volts to the conductive wall of the heating well, elevating the temperature thereof and of the mirror inserted therein. For the circuit thus described, the stainless steel wall 19 can be manufactured using a type 304 stainless steel, although this is, by no means, the only material usable.

As previously indicated, the negative temperature coefficient thermistor 54 can be placed adjacent the conductive wall to adjust the time constant for elevated temperature due to previous heating cycles.

The apparatus thus described provides a low "thermal mass" rapid heater, capable of delivering a high heat output within 3-4 seconds, the heater being touchable by the mirror for rapid heat transfer. The heater is safely electrically isolated and is essentially burn out proof. An ambient temperature sensing function is included to continuously update the heat cycle in accordance with the stored heat in the heating well. A positive cutoff function is provided whether or not the mirror is left in the heating cavity, thereby preventing overheating of the mirror. Furthermore, the trigger circuit is essentially immune to the insertion of objects other than highly reflective devices and will not respond to insertion of such objects as a child's finger and, in fact, will not respond to a dirty mirror. The circuit furthermore exhibits extremely low standby current drain because the primary circuit of transformer 25 is only completed during an actual heat cycle.

While one advantageous embodiment has been chosen to illustrate the invention it will be understood by those skilled in the art that various changes and modifications can be made therein without departing from the scope of the invention as defined in the appended claims.

What is claimed is:

1. An apparatus for warming a dental mirror of the type having a handle and a reflective portion before use to prevent fogging thereof comprising the combination of a housing;

a heating well supported in said housing, said well having a plurality of walls, at least one of said walls being made of an electrically conductive material, said at least one wall being capable of generating heat when an electric current is passed therethrough, said well being sufficiently large to receive the reflective portion of a dental mirror and sufficiently small to keep said reflective portion in close proximity to said at least one wall;

means in said housing defining an access opening adjacent said well for permitting insertion of at least the reflective portion of said mirror into said well in heat exchange relationship to said at least one electrically conductive wall;

means connectable to a source of electrical power for providing current to said at least one conductive wall for heating said wall;

means in a wall of said well defining a light transmissive portion therethrough;

photoelectric means mounted in said housing including means for transmitting light into and receiving reflected light from the reflective portion of a mirror in said well through said light transmissive portion and for producing a control signal in response to said reflected light; and circuit means responsive to said control signal for actuating said means for providing current to said at least one conductive wall for a limited predetermined time interval.

2. An apparatus according to claim 1 wherein the material of said at least one electrically conductive wall is stainless steel.

3. An apparatus according to claim 1 wherein said circuit means includes a timing circuit having two states including a first stable state and a second temporary state;

second circuit means connected to said timing circuit and said photoelectric means for causing said timing circuit to change from the first to the second of said two states in response to said control signal to produce a trigger signal, said means for providing current being responsive to said trigger signal to supply current to said at least one conductive wall;

said timing circuit being operative to return to said first state and to terminate said trigger signal after a predetermined time interval.

4. An apparatus according to claim 3 wherein said means for providing current includes a step-down transformer having a primary winding connectable to a source of AC line voltage and a secondary winding producing a voltage significantly lower than line voltage, said secondary winding being connected to said conductive wall;

a semiconductor switching device having a control electrode and a switchable path in series circuit relationship with said primary winding and said source; and means responsive to said trigger signal and connected to said control electrode for rendering said switchable path conductive only when said timing circuit is in said second state.

5. An apparatus according to claim 1 wherein
said photoelectric means includes
a source of light arranged to direct light through said light transmissive portion into said well; and
a photoresponsive element arranged to receive reflected light from within said well through said light transmissive portion and having a conductivity characteristic which varies with light incident thereon.

* * * * *